United States Patent
Hayre et al.

(10) Patent No.: US 12,036,310 B2
(45) Date of Patent: Jul. 16, 2024

(54) SKIN REJUVENATING COMPOSITION

(71) Applicant: Endoderm Laboratories, LLC, Great Falls, VA (US)

(72) Inventors: Nicole Hayre, Great Falls, VA (US); John E. Kulesza, Wethersfield, CT (US)

(73) Assignee: Endoderm Laboratories, LLC, Great Falls, VA (US)

( * ) Notice: Subject to any disclaimer, the term of this patent is extended or adjusted under 35 U.S.C. 154(b) by 0 days.

(21) Appl. No.: 17/128,847

(22) Filed: Dec. 21, 2020

(65) Prior Publication Data

US 2021/0186857 A1   Jun. 24, 2021

Related U.S. Application Data

(60) Provisional application No. 62/951,462, filed on Dec. 20, 2019.

(51) Int. Cl.

| | | |
|---|---|---|
| A61K 36/00 | (2006.01) | |
| A61K 8/63 | (2006.01) | |
| A61K 8/64 | (2006.01) | |
| A61K 8/67 | (2006.01) | |
| A61K 8/9789 | (2017.01) | |
| A61Q 19/08 | (2006.01) | |

(52) U.S. Cl.
CPC .............. *A61K 8/9789* (2017.08); *A61K 8/63* (2013.01); *A61K 8/64* (2013.01); *A61K 8/671* (2013.01); *A61K 8/676* (2013.01); *A61K 8/678* (2013.01); *A61Q 19/08* (2013.01)

(58) Field of Classification Search
CPC .................................................... A61Q 19/08
See application file for complete search history.

(56) References Cited

U.S. PATENT DOCUMENTS

2019/0240141 A1 *   8/2019   Boland ................. A61K 8/733

FOREIGN PATENT DOCUMENTS

| CN | 101756872 A | * | 6/2010 | |
|---|---|---|---|---|
| HU | 201000599 A1 | * | 8/2012 | |
| JP | 2007016003 A | * | 1/2007 | |
| KR | 2019109904 A | * | 9/2019 | .......... A61K 8/9789 |
| SU | 1734751 A1 | * | 5/1992 | |

OTHER PUBLICATIONS

Khemraj et al., An updated review on Bidens pilosa L. Der Pharma Chemica (2010), vol. 2, No. 3, pp. 325-337 (Year: 2010).*
Steroids and triterpenoid from the fruit bodies of Ganoderma lucidum and their cytotoxic activity. Natural Product Sciences (2009), 15(3), 173-179 (Year: 2009).*
Shazia et al, Determination of optimum harvesting time for vitamin C, oil and mineral elements in berries sea buckthorn (*Hippophae rhamnoides*). Pakistan Journal of Botany (2010), vol. 42, No. 5, pp. 3561-3568 (Year: 2010).*
(Unknown author), Assessment report on *Capsella bursa-pastoris* (L.) Medikus, herba, European Medicines Agency, Jul. 12, 2011.
Al-Snafi, A., The chemical constituents and pharmacological effects of Capsella bursapastoris—A review, International Journal of Pharmacology & Toxicology, 5(2): 76-81, Jan. 2015.

* cited by examiner

*Primary Examiner* — Qiuwen Mi
(74) *Attorney, Agent, or Firm* — Weston R. Gould; Dinsmore & Shohl LLP (57) ABSTRACT

Provided are compositions that stimulate the oxytocin receptor in the skin of a subject thereby leading to improved skin appearance and youthfulness. Also provided are processes of rejuvenating the skin of a subject to improve a youthful appearance by application of one or more compositions as provided herein.

16 Claims, 3 Drawing Sheets

Subject 2

Subject 1

Subject 3 UV

Subject 3

FIG. 3

SKIN REJUVENATING COMPOSITION

CROSS REFERENCE TO RELATED APPLICATIONS

This application depends from and claims priority to U.S. Provisional Application No. 62/951,462 filed Dec. 20, 2019, the entire contents of which are incorporated herein by reference.

FIELD

This disclosure relates to compositions and methods for the promotion of vibrant, youthful appearing skin of a subject.

BACKGROUND

Animal skin serves essential roles in protecting an organism from environmental insults. Numerous specific skin functions include protection, excretion, secretion, absorption, thermoregulation, pigmentogenesis, accumulation, sensory perception, and regulation of immunological processes. The structural and chemical changes in the skin during ageing reduce the effectiveness of skin to achieve each of these principal functions. Furthermore, as humans age, the skin succumbs to reduced vitality, responsiveness, dulling appearance, and becomes less attractive to others of the species.

These alterations to the appearance and function of the skin are not isolated. The epidermis and central nervous system have a common embryologic origin in that both are derived directly from the ectoderm layer. This suggests that neuropeptide signaling in the skin may be linked to a person's mental state and to the self-confidence and sexuality the person exudes to others. This combined with a more youthful appearance to the skin may convey signs of fertility to the opposite sex.

Thus, there exists a need for compositions and methods of enhancing skin's youthful appearance.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Provided are compositions for improving the appearance of skin and reduction of visible age and/or solar damage. Compositions include one or more bioactive agents capable of stimulating an oxytocin receptor in the epidermis of a subject alone or in combination with one or more additive agents not found in combination with the bioactive agent in nature, should the bioactive agent be a natural product. The compositions may be formulated for topical application to a subject. In some aspects, the bioactive agent is capable of stimulating activity of an oxytocin receptor expressed in a human fibroblast. Optionally, the bioactive agent is a cyclic peptide or a steroid, or optionally one of these agents or another bioactive agent from a plant, optionally a plant extract. A plant extract is optionally an extract of one or more portions of *O. affinis, Capsella bursa-pastoris, Bidens pilosa* L., *Oldenlandia affinis, Clitoria ternatea*, or combinations thereof.

Also provided are processes of improving the youthful appearance and or reduction of evidence of age and/or sun exposure of a subject that includes application of the compositions as provided herein to the skin of a subject. The compositions may be applied daily, optionally 1, 2, or 3 times daily, and optionally for one day or more, optionally 5 days, optionally 1 week, optionally one month, optionally indefinitely. In some aspects, a composition may be applied prior to a subject sleeping, optionally nightly.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings.

DETAILED DESCRIPTION

Provided are compositions that when applied to the skin stimulate oxytocin receptors within the epidermis that in turn prevents the normal physiological response to aging in the skin. Keratinocytes secrete oxytocin in response to an ATP analogue in a dose-dependent manner. Denda S., Takei K., Kumamoto J., et al. *Exp Dermatol* 2012: 21: 535-561. Oxytocin (OT) is a neuropeptide which is involved with milk ejection, uterine contractions, behavior, memory, social bonding, and mental state. Deing V, et al., *Exp Dermatol* 2013: 22: 399-405; Denda M., et al., *Med Hypotheses* 2013 February; 80(2):194-196; and Cho S., et al., *Br J Dermatol* 2019; 181(6): 1216-1225. In fact, both OT and its carrier protein neurophysin I are synthesized in keratinocytes. Denda S., Takei K., Kumamoto J., et al. *Exp Dermatol* 2012: 21: 535-561.

The oxytocin Receptor (OTR) is a seven-membrane spanning receptor that is coupled via various G-protein isoforms to different signaling pathways, allowing it to have various physiologic functions in different cell types. The OTR is expressed on Human Fibroblasts. Deing V., et al., *Exp Dermatol* 2013; 22:399-405; Kinsey C., et al., *J Cell Mol Med,* 2007; 11(1): 96-110. Oxytocin binding to its receptor on fibroblasts suppresses senescence-associated secretory phenotype (SASP). When not suppressed, SASP promotes a low-level chronic inflammatory state by releasing proinflammatory cytokines such as interleukin (IL)-6, IL-1, chemokines, growth factors, and extracellular matrix-remodeling proteases. This leads to aging of the skin by reducing the skin's youthful appearance. Therefore, oxytocin binding would have a protective, anti-inflammatory effect through its suppression of SASP and in turn prevents inflammatory cytokine release.

This disclosure for the first time directly links the level of oxytocin receptor stimulation in the subject with a more youthful appearance of the skin of the subject. As such, provided are compositions that include one or more bioactive agents formulated for administration directly to skin so that the desired site of action is intimately affected by the provided compositions. Bioactive agents as provided herein may be obtained from natural or synthetic sources, may be naturally derived, or artificially designed, or any combination thereof.

Compositions as provided herein include one or more bioactive agents. A "bioactive agent" is a chemical or biological molecule or combination of molecules suitable for delivery to the skin of a subject and has the function of being able to stimulate one or more activities of an oxytocin receptor. Optionally, a bioactive agent has pharmacological activity and is present for the reduction in aging processes in the skin, reduction of inflammation in the skin through an oxytocin-like pathway, and/or improving a youthful appearance to the skin of a subject.

In some aspects, a bioactive agent is isolated from a plant. The term "isolated" as used herein means that the bioactive agent is separated to some degree from the cell or region of the plant that naturally produces the bioactive agent, and separated from other components of that cell or region of the plant as it exists in nature. A bioactive agent may be substantially purified meaning that the bioactive agent is substantially free from other components of the natural source, optionally to a level where other components of the biological source are not detectable by standard techniques.

Optionally, a bioactive agent is present in a plant extract. A plant extract is a collection of one or more plant constituent compounds that have sufficiently similar physical, chemical, or other characteristic such that the method of extraction used to extract the bioactive agent also isolates these other similar plant constituents, if any. For example, an extract may be prepared with a hydrophilic or hydrophobic solvent such that only the hydrophilic or hydrophobic constituents soluble in that particular solvent type will be produced by the method of extraction. It is known that time and temperature of extraction may play a role in the constituents of the resulting extract in that some components of a plant may be soluble in a particular extract only if the time and temperature exceed a certain threshold value. Thus, the final identity of the constituent elements of the resulting plant extract depend on the nature of the solvents used in the extraction, the time of extraction, the temperature of extraction, and the presence or absence of any subsequent or prior extraction steps used to produce the resulting extract.

It was found that an extract of particular plant species include one or more components that stimulate the physiological activity of the oxytocin receptor in a cell of the skin. Illustrative examples of plant species from which a bioactive agent is derived or chemically synthesized to mimic include, but are not limited to *O. affinis, Capsella bursa-pastoris, Bidens pilosa* L., *Oldenlandia affinis, Clitoria ternatea*, or combinations thereof. In particular examples, a plant is *Capsella bursa pastoris*, which is presented herein as an example only. Optionally, the plant is *Capsella bursa-pastoris*, and excludes other plants or other oxytocin receptor stimulating bioactive components.

In some aspects, a plant extract may be obtained from various sources. *Capsella bursa-pastoris* is a flowering plant in the mustard family Brassicaceae native to eastern Europe and Asia minor but may be found in many other parts of the world. Extracts of the plants as used herein may be from the leaves, stems, or young flowering tops of the plant. Extraction may be performed by harvesting the leaves, stems, seeds, roots, or other portion of the plant and reducing them in size such as by chopping to improve solvent penetration. A typical particle size is optionally 0.5-5.0 mm, or any value or range therebetween. In some aspects, the plant portion is chopped into a powder type substance with a particle size of less than 0.5 mm. The chopped plant material is combined with a suitable extraction solvent for extraction of one or more bioactive agents.

Illustrative extraction solvents are such as water and/or a low molecular weight alcohol (e.g. C2-05 alcohol) such as ethanol. In some aspects, the solvent has a particular balance of hydrophobicity/hydrophilicity such that it may effectively extract compounds such as steroids that often have low solubility in either water or organic solvents such as oils. Other illustrative examples of extraction solvents include glycerin, propylene glycol, acetone, ethoxydiglycol, benzyl alcohol, dimethylisosorbide, ethylene glycol, ethanol, propanol, isopropanol, or other biocompatible extraction solvents.

A bioactive agent is optionally a component of a plant extract, optionally the only component of a plant extract. Time and temperature as well as the identity of the extraction solvent each affect the identity of the extracted components. For example, some components are more soluble in water than organic extraction solvents. Some components require more extraction time than others or are more readily extracted at higher temperature than others. Some plants or portions of the plants have more of the desired bioactive agent or modifiers of the extraction ability of the bioactive agent than other plant types of portions. To obtain a bioactive agent as used herein, the plant material may be combined with the solvent for an extraction time of 10 min to 36 hours. The extraction temperature is optionally the range 10° C. to 45° C. The resulting extract liquid may be separated from the solid material and filtered, optionally with a sterile filter. Optionally, the resulting extract is poured onto non-stick tray and allowed to dry at 80-90° C. Vacuum-spray dry equipment is optionally used for the drying procedure. The resulting dry extract powder may be weighed. An extraction ratio may be calculated as w/20×100% with "w" as the weight (g) of the dry extract powder. The sample and solvent ratio, heat, time, volume of solvent in the extraction may vary depending on the amount of the raw material used for extraction. In some aspects, a second extraction of plant material is performed optionally using the same extraction parameters or differing extraction parameters. Optionally, a second extraction is performed in a low molecular weight alcohol optionally of C2-C4. The first and second extraction solutions are optionally combined together and dried.

The bioactive agent is optionally present in the extract or final composition at a weight percent of 0.001 to 100 weight percent (wt %), optionally 1 to 99 wt %, or any value or range therebetween. Optionally, a bioactive agent is present in less than 30 wt %. Optionally, a bioactive agent is present at a weight percent of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.1, 0.01, 0.001, 0.0001, or any level in between or any range therein.

A bioactive agent as provided herein is optionally one or more steroids. Optionally, a bioactive agent as provided herein is a peptide or peptide mimetic, optionally a cyclic peptide. Optionally, a bioactive agent is a cyclic peptide obtained from or derived from a plant. Illustrative examples of a bioactive agent as used herein may be found in Koehbach, et al., *Proc Natl Acad Sci USA*, 2013 Dec. 24; 110(52): 21183-21188; or Gruber and O'brien, *Planta Med*, 2011 February; 77(3): 207-220.

The resulting composition includes one or more bioactive agents whereby a bioactive agent is sufficient and in sufficient quantity to stimulate the physiological activity of an oxytocin receptor. Optionally, the oxytocin receptor is stimulated by less than or equal to 0.01 to 1000 or more fold relative to that of a control by contact with the bioactive agent. Physiological activity of an oxytocin receptor is any measure as recognized in the art illustratively the coupling of one or more ligands, optionally Gq/11 or Gi proteins, internalization, or increases in downstream signaling, e.g. increase in release of prostaglandin $PGF_{2\alpha}$, reduction in inflammation, inhibition of SASP phenotype, among others or combinations thereof. Illustrative other examples of downstream signaling affects are as illustrated in Gerald Gimpl, and Falk Fahrenholz, *Physiol. Rev.*, 2001; 81(2):629-683. The bioactive agent optionally is capable of stimulating any such oxytocin receptor activity when present on a human fibroblast.

A composition as provided herein optionally has a pH between 1 or less and 8. The pH is optionally at or less than 7, optionally, at or less than 6, 5, 4, 3, 2, or 1.

A composition as provided herein may be in the form of a lotion, cream, gel, bar, serum, ointment, or in pad form. Optionally, the composition is provided as a cream, serum, pad, lotion or gel the contents of which are applied directly to the stratum corneum of a subject.

A composition as provided herein optionally includes one or more other additives that impart function that may augment the function of the bioactive agent as provided herein or may be inert with respect to augmenting the function of the bioactive agent as provided herein. Optionally, the one or more additives does not alter the function of the one or more bioactive agents as provided herein and does not stimulate one or more activities of an oxytocin receptor in the skin of a subject.

As such, a composition optionally includes one or more additive agents. Illustrative examples of an additive agent include but are not limited to: herbal extracts; acaricides; age spot and keratose removing agents; allergens; analgesics; local anesthetics; antiacne agents; antiallergic agents; anti aging agents; antibacterials; antibiotics; antiburn agents; antineoplastic and/or ophthalmic agents illustratively including 5-fluorouracil, doxorubicin, imiquimod, and sodium [o-(2,6-dichloranilino) phenyl] acetate; anti dandruff agents; antidepressants; antidermatitis agents; antiedemics; antihistamines; antihelminths; antihyperkeratolyte agents; antiinflammatory agents such as steroidal or non-steroidal anti-inflammatory agents illustratively flurbiprofen, ibuprofen, naproxen, indomethacin, glucocorticoids such as hydrocortisone, and other anti-inflammatory compounds; antilipemics; antimicrobials such as azelaic acid, erythromycin, sodium sulfacetamide, tetracycline and derivatives, and clindamycin; anti-mitotic drugs illustratively colchicine taxol and related compounds; antiproliferative agents; antioxidants; anti-wrinkle agents; antipruritics; antipsoriatic agents; antirosacea agents; anti seborrheic agents; antiseptics; anti swelling agents; antiviral agents illustratively ganciclovir, trifluorothymidine and related compounds; anti-yeast agents; astringents; aromatic molecules such as benzoyl peroxide, resorcinol, hydroquinone; topical cardiovascular agents; chemotherapeutic agents; corticosteroids; dicarboxylic acids; disinfectants; fungicides; hair growth regulators; skin growth factors illustratively TGFβ, epidermal growth factor, platelet derived growth factor, granulocyte macrophage colony stimulating factor (GM-CSF), interleukins, and others typically used for dermatological therapies; hormones; hydroxy acids; immunomodulators such as immunosuppressants and immunoregulating agents; insecticides; insect repellents; keratolytic agents; lactams; metals; metal oxides; miticides; neuropeptides; non-steroidal anti-inflammatory agents; oxidizing agents; pediculicides; photodynamic therapy agents; sanatives; scabicides; self tanning agents; skin whitening agents; vasoconstrictors; vasodilators; vitamins such as vitamin A or its derivatives, or vitamin D or its derivatives, or vitamin E or its derivatives; wound healing agents; wart removers; drugs that act on actin polymerization illustratively phalloidin, cytochlasin B and related compounds; inhibitors of dihydropyrimidine dehydrogenase (DPD), thymidine phosphorylase (TP) and/or uridine phosphorylase (UP) enzyme inhibitors; ultraviolet light (UV) filters illustratively benzophenone derivatives such as oxybenzone, octocrylene, octyl methoxycinnamate, and avobenzone; radiation proactive agents illustratively methyluracils such as 6-methyluracil and 4-methyluracil; and immunomodulating molecules such as tacrolimus, and pimecrolimus. As is known to one of skill in the art, in some instances a specific additive agent may have more than one activity, function or effect.

Optionally, an additive agent is vitamin A or its derivatives. Examples of vitamin A or its derivatives illustratively include retinoids such as retinal, retinoic acid, retinyl ester, retinol, tretinoin, isotretinoin, adapalene, tazarotene, and the like. In some aspects, a vitamin A or its derivatives are present at between 0.001 to 2 weight percent.

An additive agent is optionally vitamin E or its derivatives. Illustrative derivatives of vitamin E include sodium vitamin E phosphate, lauryl imino dipropionic acid tocopheryl phosphate, tocopheryl glucoside, tocopheryl succinate, tocophersolan (tocopheryl polyethylene glycol 1000 succinate), tocophereth-5, tocophereth-10, tocophereth-12, tocophereth-18, or tocophereth-50. Vitamin E or its derivatives are optionally present in an amount ranging from 0.1% to 10% by weight, or any value or range therebetween. The use of vitamin E or its derivatives to increase exfoliation are illustrated in U.S. Pat. No. 6,645,514.

Optionally, an additive agent includes vitamin C (ascorbic acid), optionally L-ascorbic acid, or its derivatives. Illustrative examples of vitamin C derivatives include 2- or 3-O-alkyalted ascorbic acid, 6-O-acyl-L-ascorbic acid-3-O-phosphates, tetrahexyldecyl ascorbate, sodium ascorbyl phosphate, L-ascorbyl-6-protocatechuate, L-ascorbyl-6-gallate, and L-ascorbyl-6-caffeate, 2-O-α-D-glucopyranosyl-L-ascorbic acid, 6-O-acyl-2-O-α-D-glucopyranosyl-L-ascorbic acid, magnesium ascorbyl phosphate and ascorbyl glucosamine.

The compositions as provided herein optionally include 0.005 to 1.0 weight percent retinol or derivative thereof, in which case they are optionally applied directly to the skin, or supplied as more concentrated solution containing higher levels of active agent, in which case prior to application they are diluted optionally by means of a cosmetically acceptable carrier to a desired level such as 0.005 to 1.0 weight percent for retinol.

An additive is optionally one or more antioxidants, antistatic agents, buffering agents, bulking agents, chelating agents, cleansers, colorants, conditioners, deodorants, diluents, dyes, emollients, flavonoids, fragrances, hair conditioners, humectants, ionization agents, moisturizers, occlusive agents, perfuming agents, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. The source and type of additive operable herein is readily understood by one of skill in the art. Illustrative examples of additives are found in WO 2009/090558 and references cited therein each of which are incorporated herein by reference.

A humectant, when included in a composition, helps retain moisture and also prevents rapid evaporation. Illustrative examples of humectants include propylene glycol and propylene glycol derivatives, glycerin, guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, salts of hyaluronic acid, lactamide monoethanolamine, panthanol, sorbitol, acetamide monoethanolamine and derivatives, esters, salts and mixtures thereof, as well as any suitable humectant found in Handbook of Pharmaceutical Additives published by Gower where one of ordinary skill in the art will recognize suitable humectants contained therein.

Some aspects of a composition as provided herein include one or more moisturizers. Examples of moisturizers include allantoin, petrolatum, urea, lactic acid, niacinamide, sodium PCA, shea butter, caprylic/capric/stearic triglyceride, candelilla wax, lanolin, hydrogenated oils, squalene, sodium hyaluronate and lysine PCA. Other examples may be found in the Handbook of Pharmaceutical Additives published by Gower.

Additional additives to benefit skin and its condition include ceramides, glycoceramides, pseudoceramides, sphingolipids such as sphingomyelins, cerebrosides, sulphatides, and ganglioside, sphingosines, dihydrosphingosine, phytosphingosines, and phospholipids. Illustrative examples of ceramides and glycoceramides include those described in U.S. Pat. Nos. 5,589,178, 5,661,118, and 5,688,752. Illustrative examples of pseudoceramides include those described in U.S. Pat. Nos. 5,198,210; 5,206,020; and 5,415,855.

Also provided are processes of improving the youthful appearance of the skin in a subject. Youthful skin appearance may be measured by use of the Skin Age Score (SAS) as described in Guinot C., Malvy D., Ambroisine L., et al. *Arch Dermatol* 2002 November; Vol 138: 1454-1460. It is known that the SAS trends linearly with age for those between 31 and 71. As such, the processes optionally reduce the SAS relative to prior to the application of the composition or the treatment time or duration. Optionally, the processes maintain a constant SAS in a subject for a duration where an observable increase in SAS score may be evaluated. Optionally, the processes reduce the rate of increase in SAS score relative to a control subject that did not undergo the processes or relative to the known trends in SAS score for a population, optionally as the SAS score varies as described in Guinot C., Malvy D., Ambroisine L., et al. *Arch Dermatol* 2002 November; Vol 138: 1454-1460.

A process as provided herein includes applying to the skin of a subject a composition that includes one or more bioactive agents as provided herein. The skin may be located anywhere desired on the body of the subject, but is optionally the face or portion thereof. Optionally, the composition is applied to the cheek, nose, chin, orbital region, forehead, or other desired location, or combinations thereof.

As used herein the term "subject" refers to a human, non-human primate, pig, bovine, equine, mouse, rat, guinea pig, rabbit, hamster, or other mammal. A subject is optionally in excess of 20 years of age or relative adjusted age for that of a non-human mammal. Optionally, a subject is or is in excess of 25 years of age, optionally 30, 35, 40, 35, 50, 55, 60, 65, or 70 years of age. Optionally, a subject is at or between 31 to 71 years of age.

Application of a composition as provided herein is appreciated to be topical application. A composition is optionally topically applied at least, once daily, twice daily, or three times daily. In some aspects, the composition is applied nightly (QHS) such as before a subject goes to bed. The composition is optionally applied weekly, biweekly, or monthly. Typical application times include anywhere from one to 20 weeks or more. Optionally, the compositions are formulated so as to be suitable for continued use meaning that the compositions do not suffer from undesirable side effects or toxicity. Continued use is use for an indefinite period of time without interruption. Uninterrupted use (i.e. repeated applications at about the same frequency) is possible with the compositions as provided herein. As such, an inventive processes optionally include uninterrupted use for a period of time. A period as used herein is optionally from one day to 20 weeks or more. A period is optionally indefinite.

The compositions formulated as described herein are optionally topically applied to the skin for the purposes of improving the youthful appearance of the skin of the subject to which the composition is applied. A composition is optionally applied in the areas where fine lines, wrinkles, dry or inelastic skin or large pores are observed. Optionally, a moisturizer is applied with or after application of the compositions, but in some aspects use of a moisturizer separate from the compositions as provided herein is excluded.

Optionally, a process as provided herein includes applying more than one composition of the formulations described herein to the skin of a subject. A second composition is optionally applied simultaneous with, or sequential to a first composition. It is appreciated that a third, fourth, or additional composition is optionally applied simultaneous with or sequential to another composition. A first composition and one or more additional compositions optionally differ by the concentration of bioactive agent present, or the presence or absence of one or more additives. A first period and a second or additional period are optionally 1 week to 20 weeks or more, or any value or range therebetween. A first or second period is optionally indefinite. Multiple periods are optionally separated by a rest time. A rest time is optionally one to 30 days or more. A rest period may improve the long-term benefit of the applications as it prevents a subject from acclimating to the treatment providing improved results in less overall time.

Various aspects of the present disclosure are illustrated by the following non-limiting examples. The examples are for illustrative purposes and are not a limitation on any practice of the present invention. It will be understood that variations and modifications can be made without departing from the spirit and scope of the invention. Reagents used are known to those of skill in the art who understand from which sources such agents may be obtained or how such reagents are synthesized from commercially available materials.

EXAMPLES

Example 1

The oxytocin levels in the urine and results from skin condition surveys from six female subjects aged 48-61 years old were reviewed. All were in the average range of body mass index and were non-smokers. Fitzpatrick skin types II-IV were included. No subject had undergone any cosmetic procedures such as neurotoxin injections, dermal filler injections, chemical peels, laser treatments, or any other cosmetic rejuvenation treatments in the six months prior. Data was excluded from any subject that reported using any topical or cosmetic treatments with any active ingredient such as retinoic acid, retinol, salicylic acid, glycolic acid or antioxidants. Subjects were not on any hormone supplement.

Lifetime sun exposure history reported by the subjects were studied (Table 1) and compared with representative photographs taken using a medical imaging camera and software system (Canfield Scientific, Parsippany, NJ) as is done in the normal course of treatment. A Skin Age Score (SAS) produced as described by Guinot C., Malvy D., Ambroisine L., et al. *Arch Dermatol* 2002 November; Vol 138: 1454-1460 was calculated along with a lifetime sun exposure score. Since the SAS tends to be a linear relationship with the chronologic age for those between 31 and 71 years, an estimated change of SAS was calculated assuming the subject's age as their expected SAS score:

Estimated % change of SAS=[(Subject's age−SAS)/ Subject's age]×100

The sun exposure score was calculated by assigning a value to the sun exposure questions as shown in Table 1.

TABLE 1

Sun Exposure Questions

| Question | Value Assigned |
| --- | --- |
| Do you use sunscreen daily? | Yes = 0 |
| If so, what SPF? | No = 1 |
| When did you start this habit? | |
| How much Sun did you get as a child and young adult? | Minimal = 1 |
| | Moderate = 2 |
| | Extreme = 3 |
| Have you ever used a tanning booth? | Never = 0 |
| If so, how many times? | 1-2 times = 1 |
| | 3-5 times = 2 |
| | 6 or more times = 3 |

The lifetime sun exposure questionnaire revealed that all subjects, except for subject 4, used sunblock daily and have been doing so for decades. The remainder of the questions was answered as shown in Table 2.

TABLE 2

Sun Exposure Responses

| Subject | How much Sun did you get as a child and young adult? | Have you ever used a tanning booth? If so, how many times? |
| --- | --- | --- |
| 1 | Moderate | 6 times |
| 2 | Minimal | 1 time |
| 3 | Minimal | No |
| 4 | Extreme | Often for years |
| 5 | Extreme | 5 times |
| 6 | Minimal | No |

Figure 1:
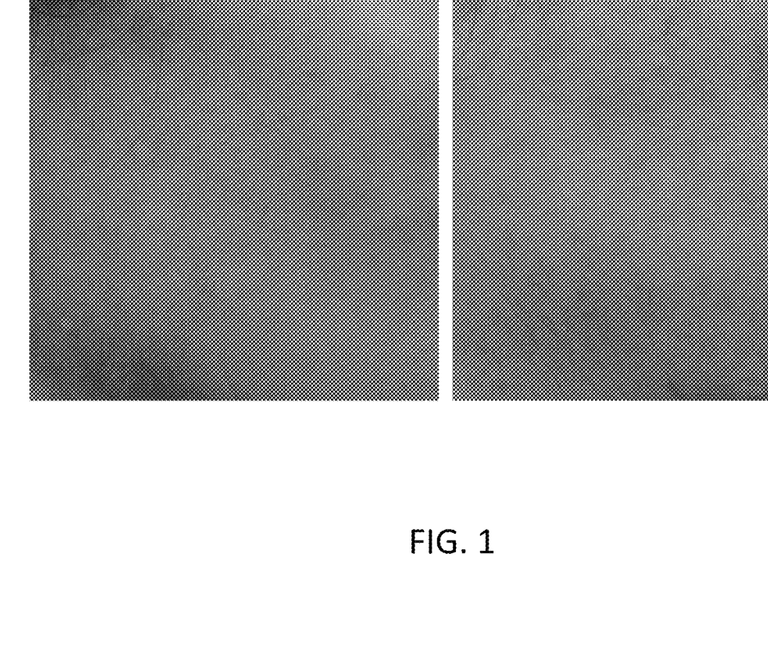
FIG. 1 illustrates in the left panel the skin appearance of Patient 5 with high oxytocin (OT) level and high estimated reduction in Skin Age Score (SAS), who reported a strong sun lifetime exposure history and in the right panel Patient 3 with a low OT level, low estimated reduction in SAS, who reported a minimal sun lifetime exposure history.

The data for oxytocin levels was a standard 24-hour amount in which subjects had collected their urine for 24 hours prior to analysis. Analysis was done by Meridian Valley Labs (Tukwila, WA). Samples were processed as per Meridian Valley Lab's protocol. Oxytocin (OT) levels ranged from 86 pmol/24 hr to 306 pmol/24 hr. SAS scores ranged from 23 to 53, and Sun exposure scores ranged from 1 to 7. (Table 3 & FIG. 1)

TABLE 3

Oxytocin Levels, Skin Age Score and Sun Exposure Score per Participant

| Subject | Age (yrs) | Fitzpatrick | OT pmol/ 24 hr | Skin Age Score | Estimated change in SAS based on age | Sun Exposure Score |
| --- | --- | --- | --- | --- | --- | --- |
| 1 | 52 | III | 216 | 28 | −46% | 5 |
| 2 | 48 | II | 101 | 34 | −29% | 2 |
| 3 | 61 | II | 115 | 53 | −13% | 1 |
| 4 | 53 | II | 120 | 47 | −11% | 7 |
| 5 | 57 | II | 306 | 23 | −60% | 5 |
| 6 | 58 | IV | 86 | 42 | −26% | 1 |

The two subjects with the highest OT levels had the greatest estimated SAS reduction in spite of having two of the highest sun exposure scores. The two subjects with the lowest reported sun exposure scores had the lowest and third lowest OT levels. They also had two of the SAS scores, which were most in line with their age, or with little reduction from the predicted value. All subjects had at least some reduction in SAS as compared to their expected score.

Figure 2:
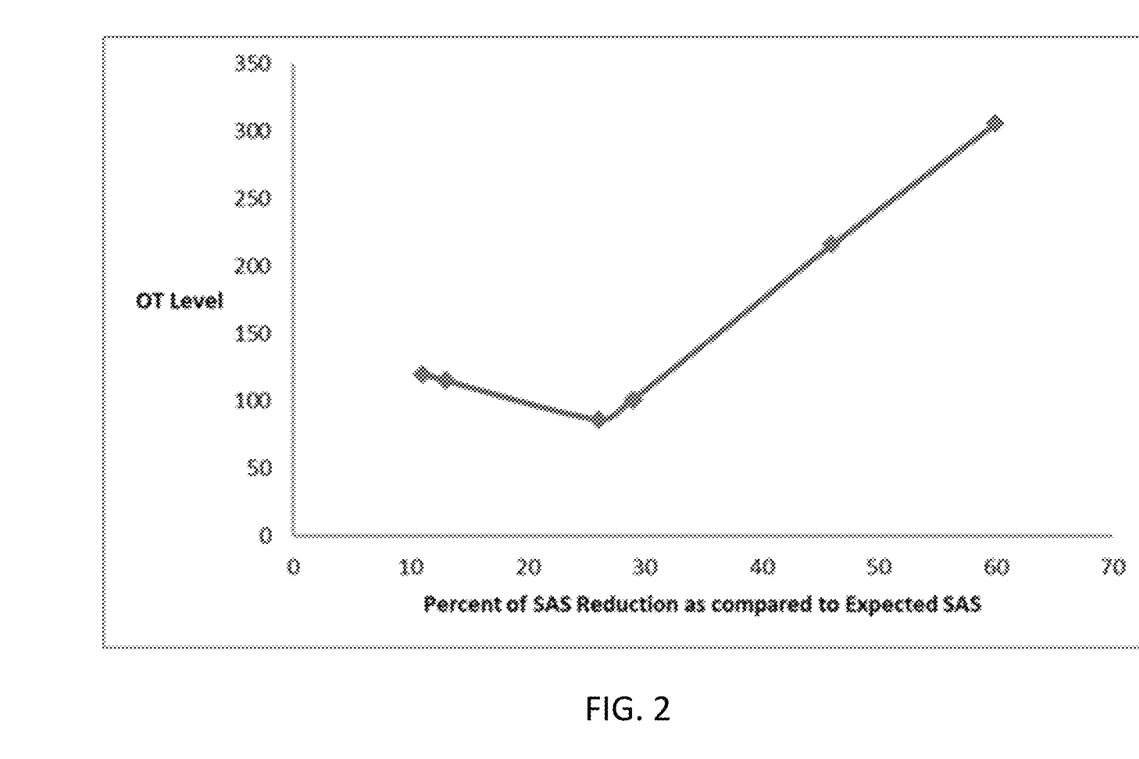
FIG. 2 illustrates a comparison of SAS reduction to OT levels (pmol/24 hr). SAS reduction was calculated using subject's actual SAS and their expected SAS. Expected SAS was assumed to correlate with the subject's age. A higher percentage of reduction corresponds to a more youthful appearing epidermis.

When the percentage of SAS reduction is plotted against the subject's OT level, the results show the higher a subject's OT level, the greater the reduction in SAS she had. (FIG. 2) This appears to be independent of the subject's lifetime sun exposure level.

Overall, this study shows that there is a clinical correlation between OT levels and the SAS of a subject. High OT levels of several patients, in spite of strong lifetime sun histories, correlated with more youthful skin and significantly lower SAS scores than expected. The reverse was also true with multiple patients whose lifetime sun histories showed a lower risk of solar damage having relatively higher SAS scores along with lower OT levels. This shows that higher levels of OT correlate with a less inflammatory environment and more youthful looking skin. This may be a protective mechanism against photo aging, intrinsic aging, or both.

Piecing all of this together leads to the conclusion that there is a complex oxytocin social exchange system that not only effects behavior, memory, social bonding, and mental state, but physiologically links each of these them to the preservation of a more youthful appearance. This more youthful appearance may in turn be interpreted by others as the subject being young, healthy and possibly a more attractive subject for social interaction. More positive social interaction and exchange of affection may in turn help to raise OT levels, thus creating a positive re-enforcement loop.

Example 2

A composition that includes a bioactive agent derived from *Capsella bursa-pastoris* is formulated as a cream for topical application to a subject with the following composition as in Table 4.

TABLE 4

Cream formulation

| Weight percent | Ingredient |
| --- | --- |
| 0.3 | Acrylic thickener (e.g. Carbomer) |
| 0.1 | Xanthan gum |

TABLE 4-continued

Cream formulation

| Weight percent | Ingredient |
|---|---|
| 1.0 | Hydrogenated lecithin |
| 3.0 | Isopropyl palmitate (IPP) |
| 3.0 | Cetearyl alcohol |
| 2.8 | Ceramide blend |
| 2.6 | Glyceryl stearate |
| 2.5 | Ceteareth-20 |
| 2.0 | Dimethicone |
| 0.1 | BHT |
| 5.0 | Vitamin C ester |
| 3.0 | Vitamin E |
| 1.0 | Salicylic acid |
| 0.1 | Retinol |
| 0.1 | Ferulic acid ester |
| 5.0 | Sodium hyaluronate |
| 3.0 | Glycerin |
| 3.0 | Niacinamide |
| 3.0 | Peptide blend |
| 1.0 | *Capsella bursa-pastoris* Extract |
| 0.6 | Melanin |
| 0.2 | Allantoin |
| qs | Preservative |
| qs | Water to complete 100 wt % total |

To formulate the Table 4 composition, a water phase is formed with the acrylic thickener and xanthan gum are dry blended then dispersed in water, which is then heated to 85° C. The hydrogenated lecithin is then added and the mixture homogenized. The mixed material is cooled with non-vortex propeller mixing.

An IPP phase is formed by intermixing isopropyl palmitate (IPP), cetearyl alcohol, ceramide blend, glyceryl stearate, ceteareth-20, dimethicone, and BHT at the appropriate amounts and heating to 72° C. with stirring. After the water phase has cooled to 70° C., the IPP phase is added to the water phase and allowed to cool.

A vitamin C ester phase is formed by mixing the vitamin C ester, vitamin E, salicylic acid, retinol, ferulic acid ester and heated to 60° C. with mixing. This is then added to the above mixture and homogenized. The remaining ingredients are mixed and heated to 50° C. then added back to the remaining batch. The final combined material is adjusted to a pH of 5.5 to 6.0 with the appropriate NaOH or HCl and cooled to room temperature for subsequent packaging.

Example 3

A first serum formula is formed for delivery of a bioactive agent derived from *Capsella bursa-pastoris* by topical application to a subject that also has the function of gentle exfoliation with application. The formulation is provided as in Table 5.

TABLE 5

Serum formulation 1

| Weight percent | Ingredient |
|---|---|
| qs | Water |
| 3.0 | Mandelic acid |
| qs pH 4.5 | Aminomethyl propanol |
| 3.0 | Potassium azeloyl diglycinate |
| 3.0 | Palmitoyl tripeptide-1, Palmitoyl tetrapeptide-7 |
| 3.0 | Panthenol |
| 2.0 | Niacinamide |
| 1.0 | *Capsella bursa-pastoris* Extract |
| 0.5 | Melanin |
| 0.2 | Allantoin |

TABLE 5-continued

Serum formulation 1

| Weight percent | Ingredient |
|---|---|
| 0.1 | Disodium EDTA |
| qs | Preservative |
| 50.0 | Sodium hyaluronate |
| qs pH 4 . . . 5-5 | Aminomethyl propanol and/or Citric acid |

The Table 5 formulation is formed by dispersing the mandelic acid into water at RT with mixing. The aminomethyl propanol is added to adjust the pH to about 4.5. The remaining ingredients are then added in the order shown in Table 5 with the exception of sodium hyaluronate and mixed until a clear solution is obtained. The sodium hyaluronate is then added and the composition mixed slowly until completely dissolved to form a thin, uniform gel with viscosity of about 20,000 centipoise (cps). The aminomethyl propanol and/or citric acid are then added to maintain the pH with the target range of 4.5-5. The composition is then packaged for delivery to a subject.

A second serum formulation is created also with the *Capsella bursa-pastoris* extract, but is designed to have a substantially neutral pH for application to the skin of subjects that are more sensitive to acids. The formulation is as in Table 6.

TABLE 6 sensitive skin serum formulation

| Weight percent | Ingredient |
|---|---|
| qs | Water |
| 3.0 | Potassium azeloyl diglycinate |
| 3.0 | Palmitoyl tripeptide-1, Palmitoyl tetrapeptide-7 |
| 3.0 | Panthenol |
| 2.0 | Niacinamide |
| 1.0 | *Capsella bursa-pastoris* Extract |
| 0.5 | Melanin |
| 0.2 | Allantoin |
| 0.1 | Disodium EDTA |
| qs | Preservative |
| 50.0 | Sodium hyaluronate |
| qs pH 4.5-5 | Aminomethyl propanol and/or Citric acid |

The Table 6 formulation is formed by combining all ingredients in the order shown in the table (with the exception of sodium hyaluronate) followed by mixing to dissolve. The sodium hyaluronate is then added and the composition mixed slowly until completely dissolved to form a thin, uniform gel with viscosity of about 20,000 centipoise (cps). The aminomethyl propanol and/or citric acid are then added to maintain the pH with the target range of 4.5-5. The composition is then packaged for delivery to a subject.

Example 4

Three subjects were studied as per the protocols of Example 1 and evaluated for skin appearance before and following daily treatment for various times with the formulation of Table 4. Subject 1 applied the composition once daily for 4 weeks. Subject 2 applied the composition once daily for 5 days. Subject 3 applied the composition once daily for 8 weeks. Sections of treated skin (before and after) were photographed using a medical imaging camera and software system (Canfield Scientific, Parsippany, NJ) as is done in the normal course of treatment. Photographs were also studied using ultraviolet (UV) enhancement. Photographs were examined for the overall appearance of the skin as well as the presence or absence of solar damage as viewed by the presence or abundance of solar lentigo or dyspigmentation. Also evaluated were pore size, dullness and rhytids (wrinkles). The SAS for all subjects was calculated prior to and following treatment using the methodology of Example 1.

Figure 3:
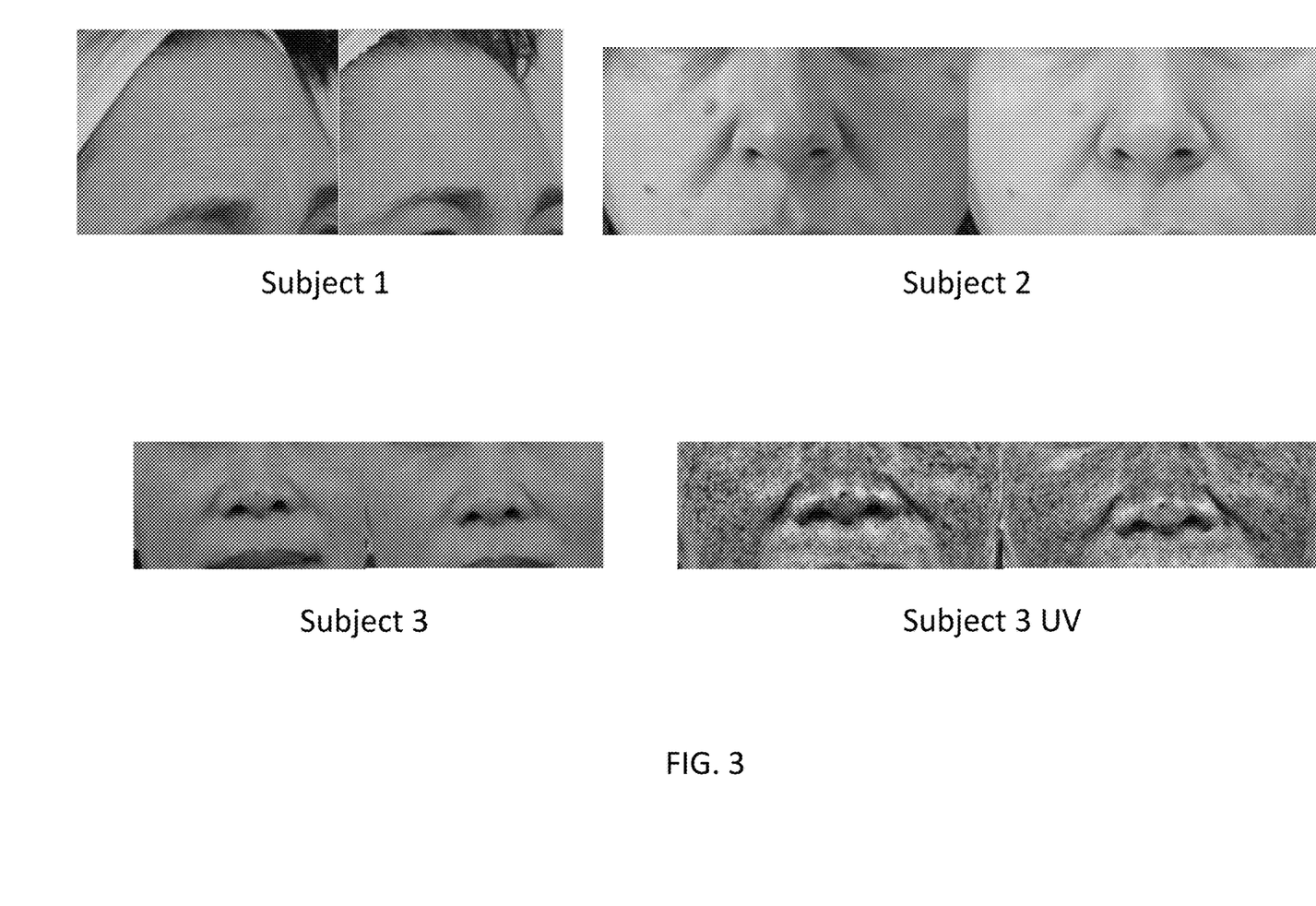
FIG. 3 illustrates photographs of human subjects treated with the formulation of Table 4 either before the treatment (left side) or following 5 days of treatment (right side) demonstrating efficacy of using the compositions as provided herein.

Results are illustrated in FIG. 3 with the before treatment sample on the left and after treatment sample on the right. All subjects tested showed an overall improvement in skin youthful appearance as is observed in a facial section of all subjects. All subjects also demonstrate a reduction in the amount of or intensity of solar lentigos of dyspigmentation in the tested sections. The SAS for each subject prior to the study and after the study demonstrates the significant improvement in appearance. Subject 1 presented with an SAS of 40 prior to the study, which improved to 26 following 4 weeks of daily application. Subject 2 presented with an SAS of 26 prior to the study, which improved to 21 following daily application for 5 days. Subject 3 presented with an SAS of 43 prior to the study, which improved to 30 following 8 weeks of daily application. These improvements are more apparent in the studies of the UV enhanced images of subject 3. Overall, these studies demonstrate that treatment of the skin with compositions that alter a subject's oxytocin level as provided herein benefits skin appearance.

The foregoing description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Various modifications of the present disclosure, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. Each patent, application or publication is incorporated herein by reference to the same extent as if each individual patent, application or publication was specifically and individually stated as incorporated herein by reference for the specific teaching for with each reference is cited and additionally for entirety of their contents including text, figures, and references.

The foregoing description is illustrative of particular aspects of the invention, but is not meant to be a limitation upon the practice thereof. The following claims, including all equivalents thereof, are intended to define the scope of the invention.

The invention claimed is:

1. A process of improving the youthful appearance of the skin in a subject comprising:
    applying a composition for topical administration to the skin of a subject, the composition comprising:
        a bioactive agent at a concentration capable of stimulating an oxytocin receptor in the epidermis of a subject, wherein the bioactive agent is a hydrophilic *Capsella bursa pastoris* plant extract; and
        one or more additive agents not found in nature combined with said bioactive agent,
    wherein the composition is formulated for topical application to a subject, and wherein the youthful appearance of the skin in said subject is improved by said applying.

2. The process of claim 1 further comprising applying said composition daily.

3. The process of claim 1 further comprising applying said composition daily for a period of twenty days or more.

4. The process of claim 1 comprising applying said composition daily for a period of 6 weeks or more.

5. The process of claim 1 where said applying is nightly.

6. The process of claim 1, wherein the bioactive agent is present at a concentration of 1 to 99 percent by weight.

7. The process of claim 1, wherein the bioactive agent is capable of stimulating activity of an oxytocin receptor expressed in a human fibroblast.

8. The process of claim 1, wherein the bioactive agent is a cyclic peptide or a steroid.

9. The process of claim 1, wherein said one or more additive agent is selected form the group consisting of: vitamin A or a derivative of vitamin A; vitamin E or a derivative of vitamin E; ascorbic acid or a derivative thereof, a hydroxy acid; benzoyl peroxide; resorcinol; an antimicrobial; an anti-neoplastic agent; an anti-viral agent; a non-steroidal anti-inflammatory agent; a UV filter; or an immunomodulator.

10. The process of claim 9, wherein said composition comprises vitamin A or its derivatives, wherein said vitamin A or its derivatives are present at 0.001 to 2 weight percent.

11. The process of claim 10, wherein said vitamin A derivative is: retinal; retinoic acid; retinyl ester; retinol; tretinoin; isotretinoin; adapalene; tazarotene; or combinations thereof.

12. The process of claim 9, wherein said composition comprises vitamin E or a derivative of vitamin E wherein said vitamin E or derivative of vitamin E is present at 0.1 to 10 weight percent.

13. The process of claim 1, wherein improving the youthful appearance of the skin comprises a reduction in Skin Age Score (SAS) of the subject.

14. The process of claim 1, wherein improving the youthful appearance of the skin comprises maintaining a constant SAS of the subject.

15. The process of claim 1, wherein improving the youthful appearance of the skin comprises reducing the rate of increase of SAS of the subject compared to a control subject.

16. The process of claim 13, wherein improving the youthful appearance of the skin further comprises an increase in oxytocin levels of the subject.

\* \* \* \* \*